United States Patent [19]

Denzel et al.

[11] 4,038,283

[45] July 26, 1977

[54] 4-ALKOXY OR HYDROXY DERIVATIVES OF 2H-PYRAZOLO[3,4-B]PYRIDINE-5-CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 732,241

[22] Filed: Oct. 14, 1976

Related U.S. Application Data

[63] Continuation-in-part of Ser. No. 573,195, April 30, 1975.

[51] Int. Cl.² ............................................. C07D 471/04
[52] U.S. Cl. ...................... 260/295.5 B; 260/268 BC; 260/293.6; 260/294.8 R; 424/251; 424/256; 424/267
[58] Field of Search .................. 260/295.5 B, 294.8 R, 260/295 F, 296 H

[56] References Cited

U.S. PATENT DOCUMENTS

| | | |
|---|---|---|
| 3,720,675 | 3/1973 | Hoehn et al. .................. 260/268 BC |
| 3,755,340 | 8/1973 | Hoehn et al. .................. 260/295.5 B |
| 3,833,598 | 9/1974 | Denzel et al. .................. 260/295 F |
| 3,850,940 | 11/1974 | Denzel et al. .................. 260/295.5 B |
| 3,856,799 | 12/1974 | Hoehn et al. .................. 260/295.5 R |
| 3,862,947 | 1/1975 | Denzel et al. .................. 260/295.5 R |
| 4,003,908 | 1/1977 | Denzel et al. .................. 260/295.5 B |

*Primary Examiner*—Alan L. Rotman
*Attorney, Agent, or Firm*—Lawrence S. Levinson; Merle J. Smith; Stephen B. Davis

[57] ABSTRACT

Compounds of the formula

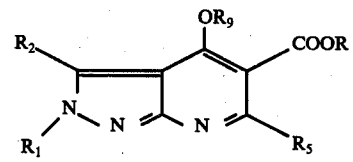

and their pharmaceutically acceptable salts wherein R is hydrogen or lower alkyl; $R_1$ is lower alkyl, phenyl or phenyl-lower alkyl; $R_2$ is hydrogen or lower alkyl; and $R_9$ is hydrogen or lower alkyl; are disclosed. These compounds are useful as antiinflammatory agents and as intermediates.

12 Claims, No Drawings

4,038,283

4-ALKOXY OR HYDROXY DERIVATIVES OF 2H-PYRAZOLO[3,4-B]PYRIDINE-5-CARBOXYLIC ACIDS AND ESTERS

This application is a continuation-in-part of Ser. No. 573,195 filed on Apr. 30, 1975.

BACKGROUND OF THE INVENTION

4-Alkoxy and hydroxy derivatives of 1H-pyrazolo[3,4-b]pyridine-5-carboxylic acids and esters are known to be useful intermediates as note Hoehn et al. in U.S. Pat. Nos. 3,755,340; 3,833,594; and 3,856,799. This invention is directed to the discovery that various 4-alkoxy and hydroxy derivatives of 2H-pyrazolo[3,4-b]pyridine-5-carboxylic acids and esters in addition to their usefulness as intermediates also possess antiinflammatory activity.

SUMMARY OF THE INVENTION

This invention relates to new alkoxy and hydroxy derivatives of 2H-pyrazolo[3,4-b]pyridine-5-carboxylic acid and esters, and acid addition salts thereof. The new compounds are of the formula

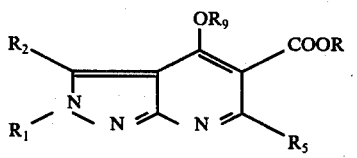

(I)

The symbols have the following meaning in formula I and throughout this specification.

R is hydrogen or lower alkyl.
$R_1$ is lower alkyl, phenyl or phenyl-lower alkyl.
$R_2$ is hydrogen or lower alkyl.
$R_5$ is hydrogen, lower alkyl, phenyl or phenyl-lower alkyl.
$R_9$ is hydrogen or lower alkyl.

The lower alkyl groups referred to throughout this specification include straight or branched chain hydrocarbon groups of one to seven carbon atoms, preferably 1 to 4 carbons. Examples of the type of groups contemplated are methyl, ethyl, n-propyl, i-propyl, n-butyl, t-butyl, etc.

The term "phenyl-lower alkyl" refers to such lower alkyl groups attached to a phenyl radical, i.e. phenylmethylene, 2-phenylethylene, etc.

The preferred compounds of formula I are those wherein:

R is hydrogen or lower alkyl of 1 to 4 carbons.
$R_1$ is lower alkyl of 1 to 4 carbons, especially methyl.
$R_2$ is hydrogen or lower alkyl of 1 to 4 carbons, especially hydrogen.
$R_9$ is hydrogen or lower alkyl of 1 to 5 carbons, especially hydrogen or ethyl.

DETAILED DESCRIPTION

The new compounds of formula I are prepared by the following series of reactions.

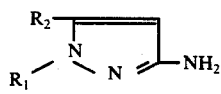

(II)

[produced analogously to the procedure described in Angew. Chem. 86, 237 (1974)] is reacted with an alkoxymethylene malonic acid dialkylester of the formula

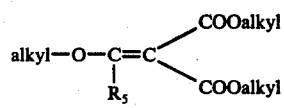

(III)

to produce a compound of the formula

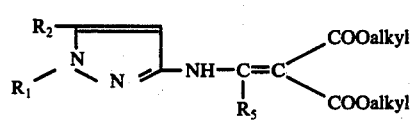

(IV)

The compound of formula IV is cyclized in an inert organic solvent such as diphenylether by heating at about 240°–260° C to produce the compound of formula I wherein $R_9$ is hydrogen.

Treatment of the compound of formula I wherein $R_9$ is hydrogen with an inorganic acid chloride or bromide such as phosphorous oxychloride, thionyl chloride, thionyl bromide, etc. yields a compound of the formula

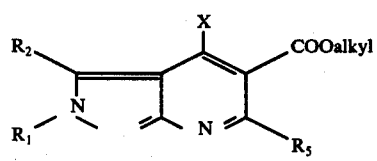

(V)

wherein X is Cl or Br. Treatment of the compound of formula V with an alcohol of formula (VI) HO-lower alkyl yields the compound of formula I wherein $R_9$ is lower alkyl.

The esters (i.e. R is lower alkyl) of formula I can be converted to the free acid by conventional means such as treatment with an organic acid such as acetic acid.

The compounds of formula I form pharmaceutically acceptable acid addition salts by reaction with equivalent amounts of the common inorganic and organic acids. Such salts include the hydrohalides, e.g., hydrobromide, hydrochloride, sulfate, nitrate, phosphate, acetate, citrate oxalate, tartrate, malate, succinate, benzoate, ascorbate, alkanesulfonate, e.g., methanesulfonate, arylsulfonate, e.g., benzenesulfonate, etc. It is frequently convenient to purify or isolate the product by forming an insoluble salt. The base may be obtained by neutralization and another salt then formed by treatment with the appropriate acid.

As disclosed in Ser. No. 573,195, the compounds of formula I are useful as intermediates in the preparation of various 4-amino derivatives of the formula

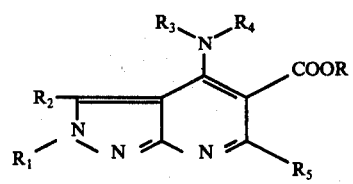

(VII)

wherein R, R₁, R₂ and R₅ are as defined above and R₃ and R₄ are independently selected from hydrogen, lower alkyl, phenyl, substituted-phenyl, phenyl-lower alkyl, (substituted-phenyl)-lower alkyl, and di(lower alkyl)amino-lower alkylene or R₃ and R₄ taken together with the N atom to which they are attached form a six membered substituted or unsubstituted saturated heterocyclic ring which may contain a second nitrogen atom. Exemplary of the heterocyclic moieties are those of the formulae

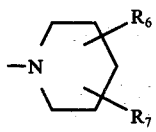 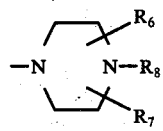

wherein R₆ is hydrogen, lower alkyl or hydroxy-lower alkyl and R₇ and R₈ are independently selected from hydrogen and lower alkyl.

The compounds of formula VII possess useful anti-inflammatory activity and are prepared by treating the 4-halo compound of formula V or the 4-alkoxy compound of formula I (i.e. R₉ is lower alkyl) with an amino compound of formula

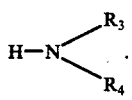

(VIII)

The compounds of formula I are useful in treating inflammation in mannalian species, e.g., rats, dogs, cats, monkeys, etc. Joint tenderness and stiffness (in conditions such as rheumatoid arthritis) are relieved by the above-described compounds.

The compound or mixture of compounds of formula I can be used as antiinflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts ranging from about 1 mg./kg./day to about 30 mg./kg./day, preferably from about 3 mg./kg./day to about 15 L mg./kg./day. A preferred unit dose for use in treating a 70 kg. mammal would contain from 210 mg. to about 1,050 mg. of active ingredient.

The following examples constitute preferred embodiments and also illustrate how these and other members of this group are produced. Simple variation of the reactants and substitution in the reaction sequences described below, readily yield other compounds within the scope of the invention. All temperatures are in degrees centigrade.

EXAMPLE 1

4-Hydroxy-2-methyl-2H-pyrazolo[3,4-b]pyridine-5-carboxylic acid, ethyl ester a. [[(1-Methyl-1H-pyrazol-3-yl)amino]methylene]-propanedicarboxylic acid, ethyl ester 194 g. (2 moles) of 3-amino-1-methyl-pyrazole and 432 g. of ethoxymethylene malonic acid, diethyl ester are stirred together for 1 hour at 100°. The alcohol formed is removed in vacuo and the resulting product crystallized from ether to yield 425 g. of [[(1-methyl-1H-pyrazol-3-yl)amino]-methylene]propane-dicarboxylic acid, ethyl ester; m.p. 60°–63°.

b. 4-Hydroxy-2-methyl-2H-pyrazolo[3,4-b]pyridine-5-carboxylic acid, ethyl ester 534 g. of the ester from part (a) are added to about 3 liters of 240° diphenylether (oil-bath temperature of 280°–290°) with stirring causing the temperature of the solvent to drop. The mixture is kept at 220° for 30 minutes while the alcohol which forms is continuously removed by distillation. The solution is cooled to about 100° and the solvent is distilled off (b.p.$_{0.04}$ 90°–95°). The oil residue is treated with 500 ml. of acetonitrile and after standing overnight the ringclosed product crystallizes. Recrystallization from n-propylalcohol yields 235 g. (67%) of 4-hydroxy-2-methyl-2H-pyrazolo[3,4-b]pyridine-4-carboxylic acid, ethyl ester; m.p. 222°–224°.

EXAMPLE 2

4-Ethoxy-2-methyl-2H-pyrazolo[3,4-b]pyridine-5-carboxylic acid, ethyl ester 221 g. (0.1 mole) of 4-hydroxy-2-methyl-2H-pyrazolo[3,4-b]pyridine-5-carboxylic acid, ethyl ester from Example 1 is refluxed with stirring for 15 hours in 1 liter of thionyl chloride. The thionyl chloride is distilled off and the residue is dissolved in about 1 liter of ethyl alcohol. On cooling, a precipitate of 270 g. of 4-ethoxy-2-methyl-2H-pyrazolo[3,4-b]pyridine-5-carboxylic acid, ethyl ester, hydrochloride; m.p. 162°–164°, is obtained.

The free base is obtained quantitatively by dissolving the hydrochloride in water and subsequently neutralizing with sodium hydroxide. The 4-ethoxy-2-methyl-2H-pyrazolo[3,4-b]pyridine-5-carboxylic acid, ethyl ester; m.p. 163°–165° (methanol); precipitates and is removed by filtration.

EXAMPLE 3

2-Methyl-4-(1-methylethoxy)-2H-pyrazolo[3,4-b]pyridine-5-carboxylic acid, ethyl ester 15 g. of 4-hydroxy-2-methyl-2H-pyrazolo[3,4-b]pyridine-5-carboxylic acid, ethyl ester from Example 1b are refluxed with stirring for 15 hours in 50 ml. of thionyl chloride. The thionyl chloride is distilled off and the residue is refluxed for one hour with 50 ml. of isopropyl alcohol. Then the isopropanol is removed in vacuo and the residue is dissolved in 10 ml. of water. This aqueous solution is made basic by the addition of aqueous sodium hydroxide and the resulting crystals are removed by filtration to yield 12 g. of 2-methyl-4-(1-methylethoxy)-2H-pyrazolo[3,4-b]-pyridine-5-carboxylic acid, ethyl ester; m.p. 107°–109° (ethylacetate).

EXAMPLES 4–7

Following the procedure of Example 2 but substituting for the ethyl alcohol the following alcohols:
methyl alcohol,
n-butyl alcohol, and
t-butyl alcohol one obtains:
4-methoxy-2-methyl-2H-pyrazolo[3,4-b]pyridine-5-carboxylic acid, ethyl ester,
4-n-butoxy-2-methyl-2H-pyrazolo[3,4-b]pyridine-5-carboxylic acid, ethyl ester,
and 4-t-butoxy-2-methyl-2H-pyrazolo[3,4-b]pyridine-5-carboxylic acid, ethyl ester respectively.

EXAMPLES 8-19

Following the procedure of Example 1 but employing the substituted pyrazole shown below in Col. I and the alkoxymethylene malonic acid dialkyl ester shown below in Col. II, one obtains the hydroxy compounds shown in Col. III which are converted by the process set forth in Example 2 to the alkoxy compounds of Col. IV.

| | Col. I | Col. II | Col. III | Col. IV |
|---|---|---|---|---|
| | $R_2$-pyrazole-$R_1$-$NH_2$ | alkyl—O—C=C($R_5$)(COOalkyl)(COOalkyl) | OH-substituted pyrazolo[3,4-b]pyridine with COOalkyl, $R_5$ | $OC_2H_5$-substituted pyrazolo[3,4-b]pyridine with COOalkyl, $R_5$ |

| Ex. | $R_1$ | $R_2$ | $R_5$ | alkyl |
|---|---|---|---|---|
| 8 | $C_2H_5$ | $CH_3$ | H | $C_2H_5$ |
| 9 | $n\text{-}C_3H_7$ | H | $CH_3$ | $CH_3$ |
| 10 | $i\text{-}C_3H_7$ | H | $C_2H_5$ | $C_2H_5$ |
| 11 | $t\text{-}C_4H_9$ | H | H | $CH_3$ |
| 12 | $n\text{-}C_4H_9$ | H | H | $C_2H_5$ |
| 13 | $CH_3$ | $CH_3$ | $i\text{-}C_3H_7$ | $C_2H_5$ |
| 14 | $CH_3$ | $C_2H_5$ | H | $n\text{-}C_3H_7$ |
| 15 | $CH_3$ | $i\text{-}C_3H_7$ | H | $t\text{-}C_4H_9$ |
| 16 | $CH_3$ | $t\text{-}C_4H_9$ | H | $C_2H_5$ |
| 17 | $CH_3$ | H | —C$_6$H$_5$ | $C_2H_5$ |
| 18 | $C_2H_5$ | H | —CH$_2$—C$_6$H$_5$ | $C_2H_5$ |
| 19 | $CH_3$ | $CH_3$ | —(CH$_2$)$_2$—C$_6$H$_5$ | $C_2H_5$ |

Similarly by employing the alcohols of examples 3-7 other compounds within the scope of the invention are obtained.

EXAMPLE 20

4-Ethoxy-2-methyl-2H-pyrazolo[3,4-b]pyridine-5-carboxylic acid 28.5 g. of 4-ethoxy-2-methyl-2H-pyrazolo[3,4-b]pyridine-5-carboxylic acid, ethyl ester, hydrochloride from Example 2 and 15 g. of potassium hydroxide are refluxed in 100 ml. of ethanol for 10 hours. The solvent is then distilled off and the residue is dissolved in 20 ml. of water. Acetic acid is added and a precipitate of 16 g. of 4-ethoxy-2-methyl-2H-pyrazolo[3,4-b]pyridine-5-carboxylic acid; m.p. 222°-225° (DMF); is obtained.

Similarly, the esters of examples 3-7 and of Col. IV of examples 8-19 can be converted to the free acid.

EXAMPLE 21

4-[(3-Dimethylaminopropyl)amino]-2-methyl-2H-pyrazolo[3,4-b]-pyridine-5-carboxylic acid, ethyl ester 2.9 (0.01 mole) of 4-ethoxy-2-methyl-2H-pyrazolo[3,4-b]-pyridine-5-carboxylic acid, ethyl ester, hydrochloride from Example 2 and 10 ml. of (3-dimethylaminopropyl)amine are refluxed for 3 hours. The excess of amine is removed in vacuo and the residue is treated with 10 ml of cold water. 2.3 g. of 4-[(3-dimethylaminopropyl)amino]-2-methyl-2H-pyrazolo[3,4-b]-pyridine-5-carboxylic acid, ethyl ester; m.p. 61°-63° (methanol/water); is removed by filtration.

EXAMPLE 22

4-(Methylamino)-2-methyl-2H-pyrazolo[3,4-b]pyridine-5-carboxylic acid, ethyl ester Following the procedure of Example 21 but substituting methylamine for the (3-dimethylaminopropyl)amine, one obtains 4-methylamino-2-methyl-2H-pyrazolo[3,4-b]pyridine-5-carboxylic acid, ethyl ester; m.p. 178°-180° (methanol/water).

EXAMPLE 23

4-(n-Butylamino)-2-methly-2H-pyrazolo[3,4-b]pyridine-5-carboxylic acid, ethyl ester Following the procedure of Example 21 but substituting n-butylamine for the (3-dimethylaminopropyl)amine, one obtains 4-(n-butylamino)-2-methyl-2H-pyrazolo[3,4-b]pyridine-5-carboxylic acid, ethyl ester; m.p. 95°-97° (methanol/water).

EXAMPLE 24

4-[(1-Methylpropyl)amino]-2-methyl-2H-pyrazolo[3,4-b]pyridine-5-carboxylic acid, ethyl ester Following the procedure of Example 21 but substituting (1-methylpropyl)amine for the (3-dimethylaminopropyl)amine, one obtains 4-[(1-methylpropyl)amino]-2-methyl-2H-pyrazolo-[3,4-b]pyridine-5-carboxylic acid, ethyl ester; m.p. 132°-134° (methanol/water).

EXAMPLE 25

4-[(1-Methylethyl)amino]-2-methyl-2H pyrazolo[3,4-b]pyridine 5-carboxylic acid, ethyl ester Following the procedure of example 21 but substituting (1-methylethyl)amine for the (3-dimethylaminopropyl)amine, one obtains 4-](1-methylethyl)amino]-2-methyl-2H-pyrazolo [3,4-b]pyridine-5-carboxylic acid, ethyl ester; m.p. 168°-170° (methanol/water).

EXAMPLE 26-49

Following the procedure of example 21 but substituting the amines shown below in Col. I for the (3-dimethylaminopropyl)amine, one obtains the products shown below in Col. II.

| | Col. I<br>H—N(R₃)(R₄) | Col. II<br>2-methyl-pyrazolo[3,4-b]pyridine with N(R₃)(R₄) at 4-position and COOC₂H₅ at 5-position |
|---|---|---|
| Ex. | R₃ | R₄ |
| 26 | H | H |
| 27 | C₂H₅ | H |
| 28 | n-C₃H₇ | H |
| 29 | n-C₅H₁₁ | H |
| 30 | CH₂—CH(CH₃)—CH₃ | H |
| 31 | —C—(CH₃)₃ | H |
| 32 | CH₃ | CH₃ |
| 33 | C₂H₅ | CH₃ |
| 34 | C₂H₅ | C₂H₅ |
| 35 | n-C₄H₉ | CH₃ |
| 36 | —C₆H₅ (phenyl) | H |
| 37 | —C₆H₄—C₂H₅ | CH₃ |
| 38 | —C₆H₃(CH₃)₂ (3,5-dimethylphenyl) | H |
| 39 | —C₆H₄—CF₃ | CH₃ |
| 40 | —C₆H₄—COOH | H |
| 41 | —C₆H₅ | —C₆H₅ |
| 42 | —CH₂—C₆H₅ | H |
| 43 | —CH₂—C₆H₄—CH₃ | H |
| 44 | —(CH₂)₂—C₆H₅ | H |
| 45 | —(CH₂)₂—C₆H₄—CF₃ | H |
| 46 | —(CH₂)₂—N(CH₃)₂ | H |
| 47 | —CH₂—CH(CH₃)—CH₂—N(C₂H₅)₂ | H |
| 48 | —CH₂—N(C₃H₇)₂ | CH₃ |
| 49 | —(CH₂)₄—N(CH₃)₂ | H |

Similarly, by also employing the compounds of Col. IV of examples 8–19 in the procedure of examples 21–49, other compounds within the scope of the invention are obtained.

EXAMPLE 50

2-Methyl-4-(1-piperidinyl)-2H-pyrazolo[3,4-b]pyridine-5carboxylic acid, ethyl ester Following the procedure of example 21 but substituting piperidine for the (3-dimethylaminopropyl)amine, one obtains 2-methyl-4-(1-piperidinyl)-2H-pyrazolo[3,4-b]pyridine-5carboxylic acid, ethyl ester; m.p. 185°–188° (methanol/water).

EXAMPLE 51

2-Methyl-4-(4-methyl-1-piperazinyl)-2H-pyrazolo]3,4-b]pyridine 5-carboxylic acid, ethyl ester Following the procedure of example 21 but substituting N-methylpiperazine for the (3-dimethylaminopropyl)amine, one obtains 2-methyl-4-(4-methyl-1-piperazinyl)-2H-pyrazolo[3,4-b]-pyridine-5-carboxylic acid, ethyl ester; m.p. 142°–143° (ethyl acetate).

EXAMPLES 52–69

Following the procedure of Example 21 but substituting the heterocyclic compound listed below for the (3-dimethylamino-propyl)amine, one obtains final products of the formula

| Ex. | HN(R₃)(R₄) |
|---|---|
| 52 | HN⌒NH (piperazine) |
| 53 | HN⌒N—C₂H₅ |
| 54 | HN⌒N—C₃H₇ |
| 55 | HN⌒N—C₄H₉ |
| 56 | HN⌒ ring with CH₃ |
| 57 | HN⌒ ring with C₃H₇ |
| 58 | HN⌒ ring with C₂H₅ |
| 59 | HN⌒ ring with C₄H₉ |
| 60 | HN⌒ ring with CH₂OH |
| 61 | HN⌒ ring with CH₃ and CH₂—CH₂OH |
| 62 | HN⌒ ring with CH₃ and CH₂—CH(OH)—CH₃ |
| 63 | HN⌒ ring with two CH₃ groups |
| 64 | HN⌒N—CH₃ with C₂H₅ |
| 65 | HN⌒N—CH₃ with C₂H₅ |
| 66 | HN⌒N—H with CH₃ and CH₃ |
| 67 | HN⌒NH with CH₂OH |
| 68 | HN⌒N—CH₃ with CH₂—CH₂OH |
| 69 | HN⌒N—CH₃ with CH₃ and CH₃ |

Similarly, by also employing the compounds of Col. IV of examples 8–19 in the procedure of examples 50–69, other compounds within the scope of the invention are obtained.

EXAMPLE 70

2-Methyl-4-(3-methylbutoxy)-2H-pyrazolo[3,4-b]pyridine-5-carboxylic acid, ethyl ester Following the procedure of Example 3 but substituting 3-methyl-butan-1-ol for the isopropanol one obtains 2-methyl-4-(3-methylbutoxy)-2H-pyrazolo[3,4-b]pyridine-5-carboxylic acid, ethyl ester; m.p. 100°-102° (ethylacetate).

EXAMPLE 71

4-Ethoxy-2-ethyl-2H-pyrazolo[3,4-b]pyridine-5-carboxylic acid, ethyl ester a. [[(1-Ethyl-1H-pyrazol-3-yl)amino]methylene]-propane-dicarboxylic acid ethyl ester 3-Amino-1-ethyl-pyrazole is substituted for the 3-amino-1-methyl-pyrazole in Example 1(a) to yield [[(1-ethyl-1H-pyrazol-3-yl)amino]methlylene]propane-dicarboxylic acid, ethyl ester; m.p. 38°-40° (ether).

b. 2-Ethyl-4-hydroxy-2H-pyrazolo[3,4-b]pyridine-5-carboxylic acid, ethyl ester 28 g. of the ester from part (a) are added to 100 ml. of 240° diphenylether (oil-bath temperature of 280° to 290°) with stirring causing the temperature of the solvent to drop. The solution is maintained at 220° for 30 minutes while the alcohol which forms is continuously removed by distillation in vacuo (b.p.$_{0.04}$, 90°-95°). The crystalline residue is recrystallized from propanol to yield 18 g. of 2-ethyl-4-hydroxy-2H-pyrazolo[3,4-b]-pyridine-5-carboxylic acid, ethyl ester as the monohydrate; m.p. 197°-198°.

c. 4-Ethoxy-2-ethyl-2H-pyrazolo[3,4-b]pyridine-5-carboxylic acid, ethyl ester

The ethyl ester product from part (b) is treated according to the procedure of Example 2 to yield 4-ethoxy-2-ethyl-2H-pyrazolo[3,4-b]pyridine-5-carboxylic acid, ethyl ester; m.p. 111°-113° (ethyl acetate).

What is claimed is:

1. A compound of the formula

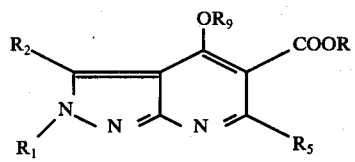

wherein R is hydrogen or lower alkyl; $R_1$ is lower alkyl, phenyl, or phenyl-lower alkyl; $R_2$ is hydrogen or lower alkyl; $R_5$ is hydrogen, lower alkyl, phenyl or phenyl-lower alkyl; $R_9$ is hydrogen or lower alkyl; and the pharmaceutically acceptable salt thereof.

2. The compound of claim 1 wherein R is hydrogen or lower alkyl of 1-4 carbons; $R_1$ is lower alkyl of 1-4 carbons; $R_5$ is hydrogen or lower alkyl of 1-4 carbons; and $R_9$ is hydrogen or lower alkyl or 1-5 carbons.

3. The compound of claim 2 wherein $R_9$ is hydrogen.

4. The compound of claim 3 wherein R is ethyl, $R_1$ is methyl; and $R_2$ and $R_5$ are both hydrogen.

5. The compound of claim 3 wherein R and $R_1$ are both ethyl; and $R_2$ and $R_5$ are both hydrogen.

6. The compound of claim 2 wherein $R_9$ is lower alkyl of 1 to 5 carbons.

7. The compound of claim 6 wherein R is ethyl; $R_1$ is methyl; $R_2$ and $R_5$ are hydrogen; and $R_9$ is ethyl.

8. The hydrochloride salt of claim 7.

9. The compound of claim 6 wherein R, $R_2$ and $R_5$ are hydrogen; $R_1$ is methyl and $R_9$ is ethyl.

10. The compound of claim 6 wherein R is ethyl; $R_1$ is methyl; $R_2$ and $R_5$ are hydrogen; and $R_9$ is isopropyl.

11. The compound of claim 6 wherein R is ethyl; $R_1$ is methyl; $R_2$ and $R_5$ are hydrogen; and $R_9$ is

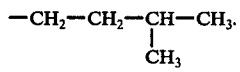

12. The compound of claim 6 wherein R, $R_1$, and $R_9$ are all ethyl; and $R_2$ and $R_9$ are both hydrogen.

* * * * *

UNITED STATES PATENT AND TRADEMARK OFFICE
CERTIFICATE OF CORRECTION

PATENT NO. : 4,038,283

DATED : July 26, 1977

INVENTOR(S) : Theodor Denzel, et al.

It is certified that error appears in the above-identified patent and that said Letters Patent are hereby corrected as shown below:

Col. 1, line 63, insert the following before formula (II):
    -- A 3-aminopyrazole of the formula --.

Col. 3, line 47, "15L mg./kg./day." should read --15 mg./kg./day.--.

Col. 6, line 60, "amine, one obtains 4-]" should read
    -- amine, one obtains 4-[ --.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks